United States Patent [19]

Cafaro

[11] Patent Number: 5,170,525
[45] Date of Patent: Dec. 15, 1992

[54] BATTERY OPERATED TOOTHBRUSH

[75] Inventor: Michael Cafaro, Quebec, Canada

[73] Assignee: Giovest Inc., Montreal, Canada

[21] Appl. No.: 708,506

[22] Filed: May 31, 1991

[51] Int. Cl.⁵ .................. A61C 17/26; A46B 13/02; A46B 7/08
[52] U.S. Cl. ........................................ 15/28; 15/180
[58] Field of Search ............... 15/28, 29, 180, 22.1

[56] References Cited

U.S. PATENT DOCUMENTS

| | | | |
|---|---|---|---|
| 2,140,307 | 12/1938 | Belaschk et al. | 15/28 |
| 3,195,537 | 7/1965 | Blasi | 15/29 |
| 3,533,119 | 10/1970 | Dokos | 15/22.1 |
| 4,698,869 | 10/1987 | Mierau et al. | |
| 4,709,438 | 12/1987 | de Tavares | |
| 4,726,806 | 2/1988 | Hukuba | |
| 4,731,896 | 3/1988 | de La Tour | |

FOREIGN PATENT DOCUMENTS 1082408  7/1980  Canada.
452961  9/1936  United Kingdom ............ 15/28

Primary Examiner—Edward L. Roberts
Attorney, Agent, or Firm—Fishman, Dionne & Cantor

[57] ABSTRACT

A brush member has two ends and includes a brush portion at one end, the brush portion including a plurality of bristles extending outwardly. A gripping member houses a motor and includes a drive rod connected to the shaft of the motor for rotatably driving the bristles, the brush member being detachably attached to the gripping member. A battery case houses a rechargeable battery and a recharging circuit for recharging the rechargeable battery. The battery case is detachably attached to the other end of the gripping member whereby electric power is provided from the battery to the motor for driving the motor. When travelling, the brush member, gripping member and battery case are detached from each other and are conveniently stored in a travel case.

6 Claims, 3 Drawing Sheets

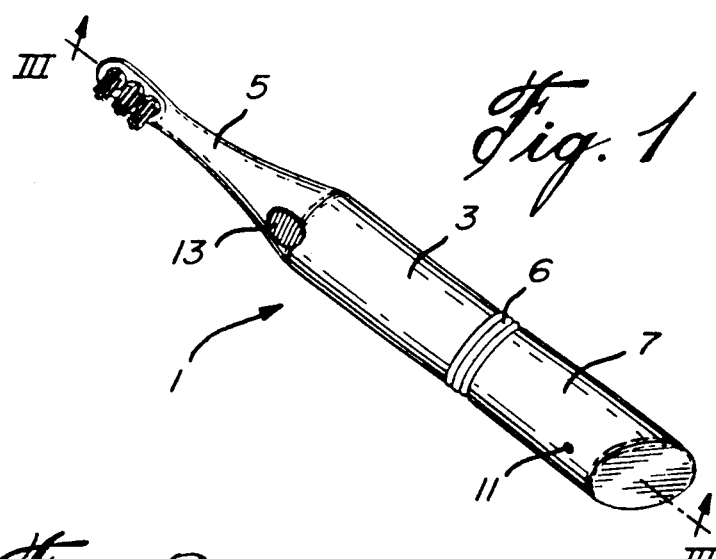
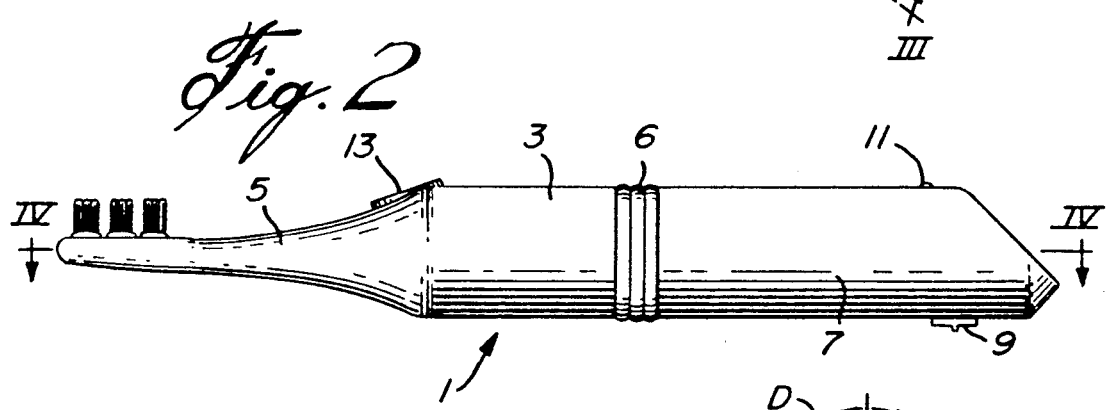
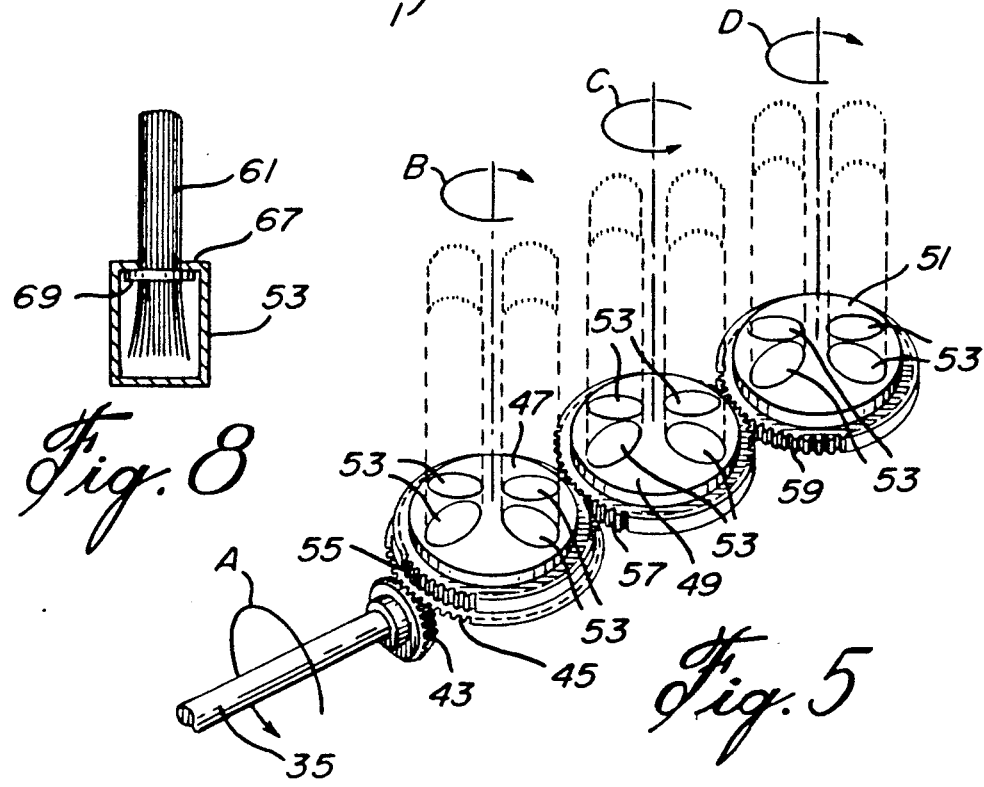

BATTERY OPERATED TOOTHBRUSH

BACKGROUND OF INVENTION

1. Field of the Invention

The invention relates to a battery operated toothbrush arrangement. More specifically, the invention relates to such an arrangement including a rechargeable battery and circuitry for recharging the rechargeable battery as well as a novel recharging arrangement for recharging the rechargeable battery.

The invention also relates to an electrically operated toothbrush having a brush including a plurality of tuft means, and a drive arrangement for rotatably driving said tuft means.

2. Description of Prior Art

Battery operated toothbrushes are known in the art as illustrated in, for example, U.S. Pat. Nos. 4,726,806, Hukuba, Feb. 23, 1988, 4,698,869, Mierau et al, Oct. 13, 1987, 4,709,438, de Tavares, Dec. 1, 1987 and 4,731,896, de La Tour, Mar. 22, 1988 as well as Canadian Patent 1,082,408, Clemens, Jul. 29, 1980.

The '806 patent teaches a battery operated toothbrush which has a battery 15 contained in the grip or handle portion 1. The head portion 3, containing bristles 7, is removable from the handle portion.

The '869 patent also teaches a battery operated toothbrush which senses the pressure applied to the teeth and transmits a signal representative of the sensed pressure. The battery 3 operates a motor 2 which has its rotary motion converted to oscillatory motion of a shaft 5 by a gear 4.

The '438 patent once again teaches a battery operated toothbrush which has a cylindrical brush 2 (see FIG. 5) which is rotated by a shaft 8 of a motor 4. The motor 4 is powered by battery 5. A gravity control switch 7 ensures that the brush always rotates in a direction from the gums to the crown of the teeth.

None of the '806, '869 or '438 patents teach a system for recharging the batteries which drive them. Indeed, it is not stated that the batteries which drive the battery operated toothbrushes of the above three patents are preferably or otherwise rechargeable.

The toothbrush of the '896 patent is not battery operated, but does have teachings of a toothbrush head 31 which is pivotable relative to the grip 5.

Canadian Patent 1,082,408 also teaches a battery operated toothbrush. However, once again, the battery is not indicated as being a rechargeable battery. The Canadian patent also teaches a gear train arrangement for rotatably driving bristle means 42 of a brush. In the Canadian patent, each bristle means is separately rotatably driven about its own central axis.

Also known in the art are rechargeable toothbrush arrangements including a recharging stand. The rechargeable batteries of the toothbrush are carried in the gripping member of the toothbrush. In order to recharge the batteries, the gripping member has to be plugged into a recharging stand which includes recharging circuitry. The recharging stand is then plugged into a power mains.

SUMMARY OF INVENTION

It is an object of the invention to provide a battery operated toothbrush having a rechargeable battery.

It is a further object of the invention to provide such a toothbrush which includes a recharging arrangement for recharging the battery.

It is a still further object of the invention to provide a battery operated toothbrush and providing means for rotatably driving the bristle means of a brush wherein a plurality of bristle means are rotatably driven about a rotating axis which rotating axis is different from the central axis of at least one of said bristle means.

It is a still further object of the invention to provide a rechargeable toothbrush having a removable and replaceable brush carrying portion.

In accordance with a feature of the invention, the battery recharging arrangement comprises a battery case including circuitry for recharging the battery, plug means for plugging into the socket of a power mains, and a socket for receiving a prong to provide electrical power from the battery to a DC motor for rotatably driving the bristle means of the brush.

In accordance with a further feature of the invention, the motor shaft of the DC motor is connected to a flexible drive rod which is connected, by a gear train arrangement, to rotatably drive the bristle means of the brush.

In accordance with a particular embodiment of the invention there is provided a battery operated toothbrush arrangement, comprising:

a brush member having two ends and including a brush portion at one end thereof, said brush portion comprising a plurality of bristle means extending outwardly of said brush portion;

a gripping member having two ends and housing a motor and including rotating means connected to the shaft of said motor for rotatably driving said bristle means, said brush member being detachably attached, at the other end thereof, to one end of said gripping member;

a battery case having two ends and housing a rechargeable battery and a recharging circuit for recharging said rechargeable battery, said battery case being detachably attached, at one end thereof, to the other end of said gripping member whereby electric power is provided from said battery to said motor for driving said motor.

The rotating means may comprise an elongated flexible rod having two ends, said elongated flexible rod being detachably attached, at one end thereof, to the free end of said shaft of said motor for rotation with said shaft of said motor.

BRIEF DESCRIPTION OF DRAWINGS

The invention will be better understood by an examination of the following description, together with the accompanying drawings, in which:

FIG. 1 is a perspective bottom view of a toothbrush in accordance with the invention;

FIG. 2 is a perspective side view of a toothbrush in accordance with the invention;

FIG. 5 is a perspective view of the gear train for rotatably driving the bristle means;

FIG. 8 illustrates a receptacle for receiving bristle means.

DESCRIPTION OF PREFERRED EMBODIMENTS

Figure 3:
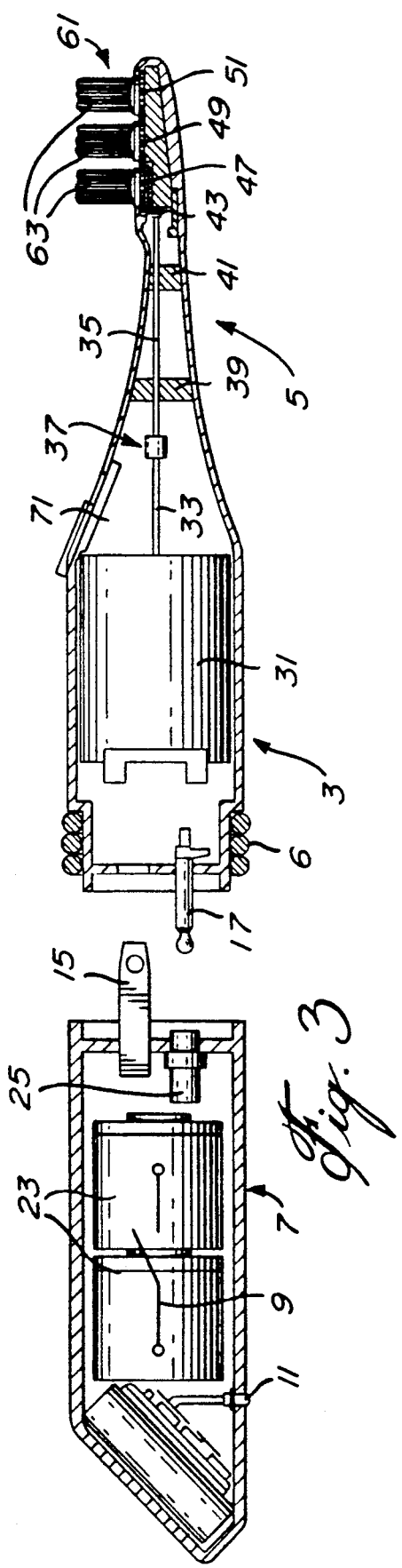
FIG. 3 is a section through III—III of FIG. 1.

Referring to FIGS. 1 and 2, the battery operated toothbrush, indicated generally at 1, comprises main body member or gripping member 3, a brush carrying member 5 and a battery case 7. The battery case 7 is detachably attached at one end of the gripping member 3, and the brush carrying member 5 is detachably attached at the other end of the gripping member 3. Bands of an elastic or rubber material are disposed between the main body member 3 and the battery case 7.

The gripping member 1, brush carrying member 5 and battery case 7 are hollow members preferably made of a plastic-like material. The elements carried within these members are described below.

ON/OFF switch 9 is provided on the battery case 7 to initiate the operation of the battery operated toothbrush, and LED ON/OFF indicator 11 is provided to show when the brush is turned ON.

A 3-speed switch 13 is provided in the gripping member to change the rotary speed of the bristle means of the brush as will be discussed below.

Figure 4:
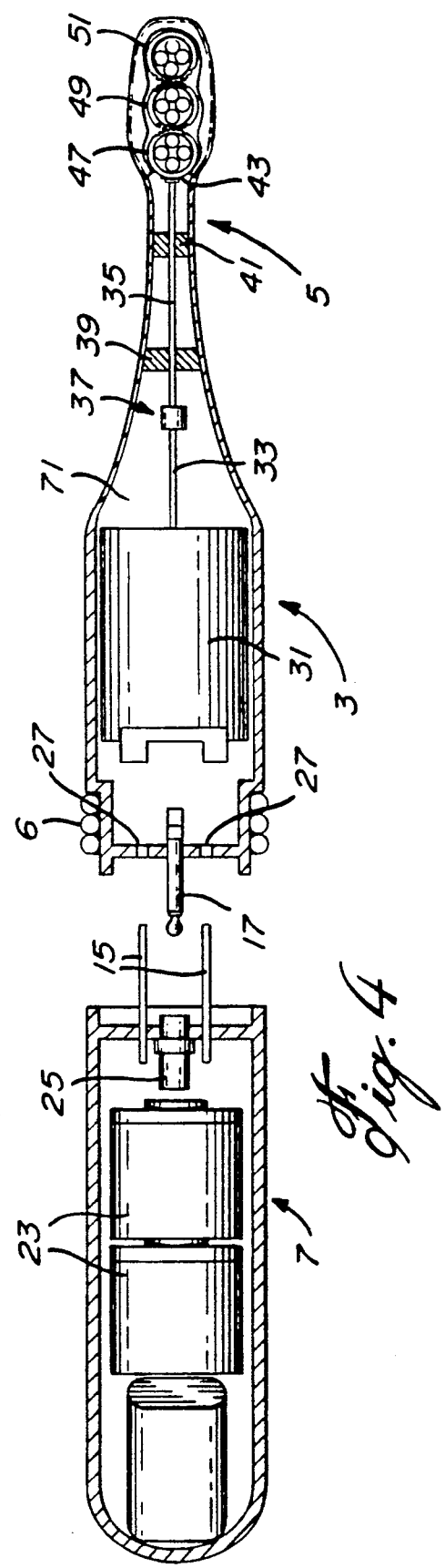
FIG. 4 is a section through IV—IV of FIG. 2.

Turning now to FIGS. 3 and 4, extending outwardly of the end of the battery case 7 adjacent to one end of the gripping member 3 are prongs 15—15. These are prongs which will be received by power mains sockets for providing electrical power in homes, hotels or the like. In North America, the power provided at the sockets is 110 volts at 60 Hz.

Extending outwardly of the end of the gripping member 3 adjacent to one end of the battery case 7 is a prong 17 which is connected, by means not shown in FIGS. 3 and 4, to the power input of the DC motor which drives the battery operated toothbrush.

Mounted in the battery case 7 are one or more rechargeable batteries 23 (two are illustrated in FIGS. 3 and 4). Preferably, the batteries are NiCa batteries. A receptacle 25, in the one end of the battery case 7 is provided for receiving the prong 17 and connecting it to the output of the rechargeable batteries 23. (The connection between receptacle 25 and the batteries is not shown in FIGS. 3 and 4).

The prongs 15—15 extend into openings 27—27 in the one end of the gripping member 3. The prongs 15—15 do not make any electrical connection when extending into the gripping member 3, but do provide support for the physical connection between battery case 7 and member 3.

ON/OFF switch 9 is schematically illustrated in FIG. 4 and LED indicator 11 is schematically illustrated in FIG. 3.

As can be seen, DC motor 31 is mounted in the main body member 3. Means (not shown in FIGS. 3 and 4) are provided to connect the probe 17 to the power input of the DC motor 31.

Extending from the side of the DC motor closest to the brush carrying member 5 is a shaft 33. Flexible rod 35 is connected to motor shaft 33 by connector means 37. The connector means 37, may comprise a snap-in quick-connect connector, or any other similar arrangement whereby the flexible rod 35 is connected for rotation with motor shaft 33 and is easily disconnectable therefrom. 39 and 41 comprise support means for the flexible rod 35.

The opposite end of the rod 35 mounts a bevel gear 43 for rotation with the rod 35. As best seen in FIG. 5, bevel gear 43 is in mating engagement with bevel gear 45 which mounts bristle disc 47 for rotation therewith. Bristle disc 49 abuts bristle disc 47, and bristle disc 51 abuts bristle disc 49. Ring gears 55, 57 and 59 are disposed around the peripheries of discs 47, 49 and 51 respectively, and gear 55 is in mating engagement with gear 57 which is in mating engagement with gear 59.

Each disc 47, 49 and 51 includes a plurality of bristle means receptacles 53 (four in FIG. 5), and, as seen in FIG. 3, brush 61 comprises a plurality of bristle means 63 held in the bristle means receptacles 53.

Figure 6:
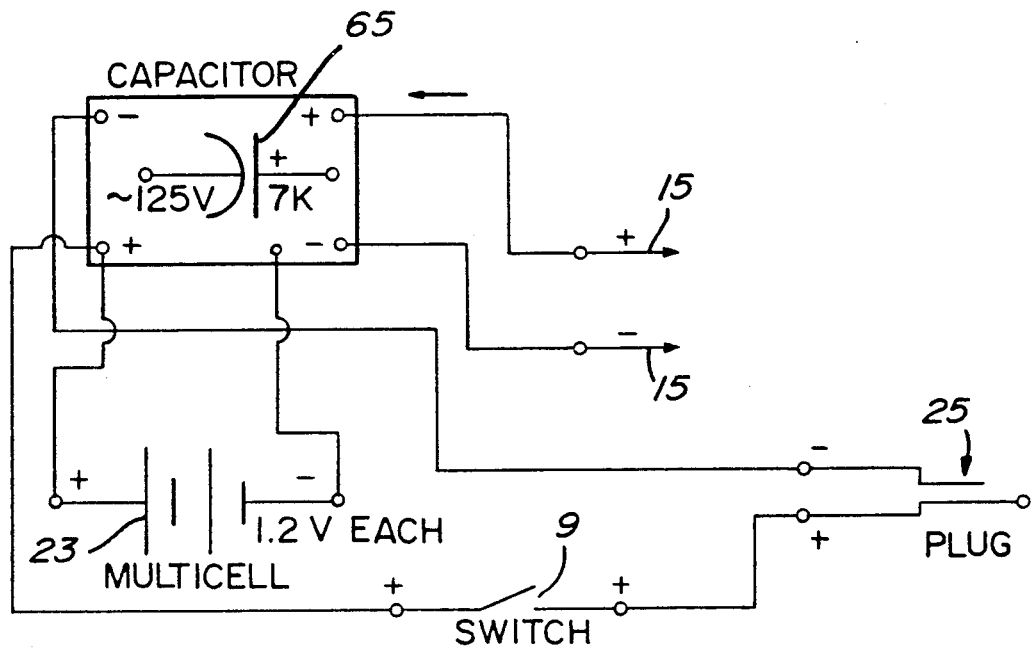
FIG. 6 is a schematic circuit diagram of the circuit for recharging the battery.

Turning now to FIG. 6, it can be seen that the recharging circuit includes a capacitor 65. When prongs 15 are inserted into a household mains socket, AC voltage is regulated by the capacitor 65 to charge the battery 23.

Figure 7:
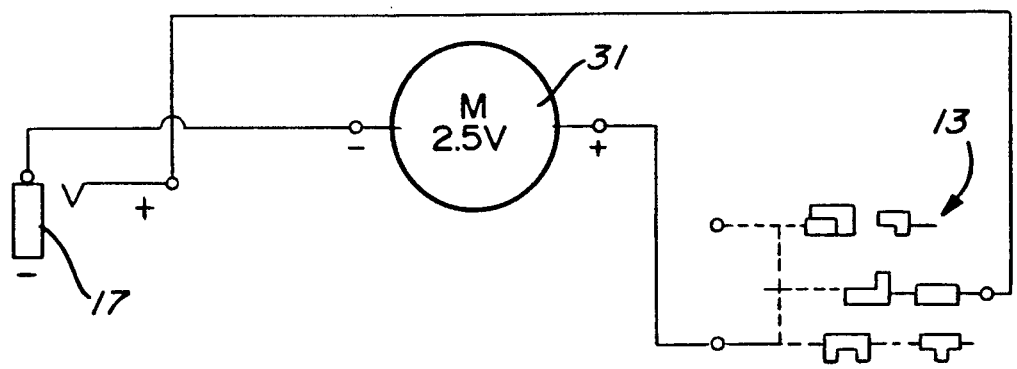
FIG. 7 is a schematic circuit diagram of the motor driving circuitry.

Considering now FIGS. 6 and 7 together, when prong 17 is inserted into receptacle 25, and switch 9 is closed, then the DC battery is connected to the motor 31. The three-position switch 13 adjusts the speed of the motor by adjusting the amount of power which reaches the motor 31.

In operation, the battery case 7 attached to the main body member 3, and the brush carrying member 5 attached to the main body member 3. When switch 9 is closed, power is applied from the battery 23 to drive the motor 31. This will cause motor shaft 33 to rotate which will, in turn, cause flexible rod 35 to rotate.

The rotary motion, about the center of the flexible rod 35, is converted to rotary motion about the center of disc 47 by bevel gear 43 and mating bevel gear 45. With the shaft rotating in the direction of arrow A, disc 47 will rotate in the direction of arrow B. Because of the interaction between gears 55 and 57, disc 49 will also rotate in the direction shown by the arrow C.

Interaction of gears 57 and 59 will cause disc 51 to rotate in the direction of arrow D.

The rotation of the bristle discs 47, 49 and 51 will cause bristle means 63 to be rotated about the central axis of their respective discs.

In a preferred embodiment, as illustrated in FIG. 8, receptacles 53 comprise a cup-like member having an annular flange 67 surrounding the free edge thereof. Bristle means 61 include an annular stop member 69 which prevents the bristle means from falling out of the cup-like receptacle, but which allows the bristle means 61 to be loosely held in the receptacle 53. With such an arrangement, when the ends of the bristle means are applied against the teeth, and pressure is applied to the toothbrush, the bristle means will begin to rotate about their own central axis. However, the direction of rotation of each bristle means about its own central axis is unpredictable.

In order to be able to use bristles of different hardnesses in the same toothbrush, and in order to be able to replace brushes when the bristle means are worn out, the brush carrying member 5 is detachably attached to the main body member 3 at the position 71 shown in FIGS. 3 and 4. The brush carrying member 5 is detachably attached to the main body member 3 by means well known in the art.

In order to recharge the battery, the battery case 7 is detached from the gripping member 3 and the prongs 15 are inserted into the socket of a household power mains. As can be seen, only a relatively small cylinder needs to be inserted into the socket, and the battery charger in effect consists of the battery case which is also the battery case for holding the battery when the entire unit is assembled.

With the inventive arrangement, the brush member 5 can be detached from the gripping portion 3 as can the battery case. The three separate parts can now be carried in a relatively small package or case so that it is convenient for travelling as compared with, for example, the prior art arrangement which requires a recharging stand.

Although a particular embodiment has been described, this was for the purpose of illustrating, but not limiting, the invention. Various modifications, which will come readily to the mind of one skilled in the art, are within the scope of the invention as defined in the appended claims.

I claim:

1. A battery operated toothbrush arrangement, comprising:
    a brush member having two ends and including a brush portion at one end thereof, said brush portion comprising a plurality of bristle means carrying discs, each bristle means carrying disc carrying bristle means extending outwardly of said brush portion;
    a gripping member having two ends and housing a motor and including rotating means connected to the shaft of said motor for rotatably driving said bristle means carrying discs, said brush member being detachably attached, at the other end thereof, to one end of said gripping member;
    a battery case having two ends and housing a rechargeable battery and a recharging circuit for recharging said rechargeable battery, said battery case being detachably attached, at one end thereof, to the other end of said gripping member whereby electric power is provided from said battery to said motor for driving said motor;
    wherein said rotating means comprises an elongated flexible rod having two ends, said elongated flexible rod being detachably attached, at one end thereof, to the free end of said shaft of said motor for rotation with said shaft of said motor;
    and wherein a bevel gear is mounted at the free end of said flexible rod for rotation therewith;
    a first one of said plurality of bristle means carrying discs mounting a disc bevel gear in mating engagement with said rod bevel gear;
    whereby, rotation of said flexible rod about the center thereof is converted to rotation of said first bristle means carrying disc about the center thereof;
    and wherein said bristle means carrying discs comprise a second bristle means carrying disc and a third bristle means carrying disc;
    each of said first, second and third bristle means carrying discs having gear means about the peripheral edge thereof;
    the gear means of said first bristle means carrying disc being in mating engagement with the gear means of said second bristle means carrying disc, and the gear means of said second bristle means carrying disc being in mating engagement with the gear means of said third bristle means carrying disc;
    whereby, rotary motion of said first bristle means carrying disc is transmitted to said second and third bristle means carrying discs;
    and wherein each of said bristle means carrying disc comprises a plurality of evenly spaced receptacles for receiving said bristle means therein;
    and wherein each receptacle comprises a cup-like member having an annular flange surrounding the free edge thereof;
    each said bristle means including an annular stop member whereby each said bristle means is loosely held in its respective receptacle.

2. An arrangement as defined in claim 1 wherein said gripping member is detachably attached to said battery case by a plug-in socket arrangement.

3. An arrangement as defined in claim 2 wherein the plug of said plug-in socket arrangement comprises a single prong extending outwardly of the second end of said gripping member, and including a mating socket, electrically connectable to said battery, in said one end of said battery case, said socket receiving said prong when said battery case is detachably attached to said gripping member, whereby, when said prong is in said socket, said prong is electrically connectable to said battery;
    said prong being electrically connected to the power input terminal of said motor;
    whereby, when said battery case is detachably attached to said gripping member, said battery is electrically connectable to said power input terminal of said motor.

4. An arrangement as defined in claim 3 and including an ON/OFF switch mounted on said battery case between said battery and said socket whereby said ON/OFF switch connects said battery to said power input of said motor in the ON position thereof and disconnects said battery from said power input of said motor in the OFF position thereof.

5. An arrangement as defined in claim 1 and including a two-pronged plug extending outwardly from said one end of said battery case, said two-pronged plug being electrically connected to said recharging circuit;
    whereby when said two-pronged plug is inserted in a power main socket, power is provided for recharging said rechargeable battery.

6. An arrangement as defined in claim 5 wherein two openings are provided in said other end of said gripping member, each opening receiving a respective prong of said two-pronged plug;
    whereby, said battery case is physically attached to said gripping member when said prongs of said two-pronged plug are inserted into said openings and said plug is inserted into said socket.

* * * * *